United States Patent
Baik et al.

(10) Patent No.: US 6,221,371 B1
(45) Date of Patent: Apr. 24, 2001

(54) PSEUDOCERAMIDES, AND DERMATOLOGIC EXTERNAL PREPARATIONS CONTAINING THE SAME

(75) Inventors: In-sub Baik; Jong-gi Lee, both of Taejon-shi; Byeong-deog Park, Chungchongbuk-do; Yoon Kim, Taejon-shi; Myung-jin Lee, Seoul, all of (KR)

(73) Assignee: Aekyung Industrial Co., Inc., Seoul (KR)

( * ) Notice: Subject to any disclaimer, the term of this patent is extended or adjusted under 35 U.S.C. 154(b) by 0 days.

(21) Appl. No.: 09/308,031
(22) PCT Filed: Nov. 10, 1997
(86) PCT No.: PCT/KR97/00220
 § 371 Date: May 10, 1999
 § 102(e) Date: May 10, 1999
(87) PCT Pub. No.: WO98/21176
 PCT Pub. Date: May 22, 1998

(30) Foreign Application Priority Data

Nov. 11, 1996 (KR) .................................................. 96-53207

(51) Int. Cl.[7] ................. A61K 6/00; A61K 7/00
(52) U.S. Cl. .................. 424/401; 424/400; 554/103; 554/108
(58) Field of Search .................... 424/400, 401; 554/1, 35, 103, 104, 105, 108

(56) References Cited

U.S. PATENT DOCUMENTS 5,221,757   6/1993   Ohashi et al. .................... 554/66

FOREIGN PATENT DOCUMENTS

| | | |
|---|---|---|
| 3334210 * | 4/1985 | (DE) . |
| 0 282 816 | 9/1988 | (EP) . |
| 698598 * | 2/1996 | (EP) . |
| 62-207247 | 9/1987 | (JP) . |
| 63-192703 | 8/1988 | (JP) . |
| 63-216812 | 9/1988 | (JP) . |
| 64-9906 | 1/1989 | (JP) . |
| 64-9907 | 1/1989 | (JP) . |
| 2-306949 | 12/1990 | (JP) . |
| WO 92/03129 | 3/1992 | (WO) . |
| WO 92/06982 | 4/1992 | (WO) . |
| WO 92/03129 | 6/1993 | (WO) . |
| 9521182 * | 8/1995 | (WO) . |
| 9601807 * | 1/1996 | (WO) . |

OTHER PUBLICATIONS

Park et al, Novel Pseudoceramides and their Synthesis Using Alkyl Ketene Dimer, Sci. Conf. Asian Soc. Cosmet. Sci., 3rd, pp. 50–54, 1997.*

Bukec, Amides of B–Keto Acids, Chem. Abstr., vol. 70, No. 5, p. 1944, Abstract No. 19609X, 1969 (Feb.).*

* cited by examiner

Primary Examiner—Dameron L. Jones
(74) Attorney, Agent, or Firm—Nath & Associates, PLLC; Gary M. Nath; Jerald L. Meyer

(57) ABSTRACT

The present invention relates to pseudoceramide derivatives represented by formula(I) or (II):

$$R_1\text{—COCHR}_2\text{CONR}_3R_4 \qquad (I)$$

$$R_1\text{—CH(OH)CHR}_2\text{CONR}_3R_4 \qquad (II)$$

wherein, each of $R_1$ and $R_2$ represents linear or branched alkyl group or alkenyl group having 6~22 carbon atoms; each of $R_3$ and $R_4$ represents hydrogen, methyl, ethyl, propyl, or linear or branched $C_2$~$C_6$ alkyl group having one or more hydroxyl group(s), or monosaccharide, a process for preparing the same, and dermatologic external preparations containing the same. When the pseudoceramide derivatives according to the present invention are applied in an dermatologic external preparations the moisture-retaining property and resilience of skin and hair is enhanced such so that the derivatives are useful in protection of skin-aging. In addition, the derivatives are useful for inducing the formation of lipid layer on damaged skin and for preventing the inhibition of lipid synthesis.

8 Claims, No Drawings

PSEUDOCERAMIDES, AND DERMATOLOGIC EXTERNAL PREPARATIONS CONTAINING THE SAME

This application is a 371 of PCT/KR97/00220, filed Nov. 10, 1997.

BACKGROUND OF THE INVENTION

1. Field of the Invention

The present invention relates to novel pseudoceramides. More specifically, it relates to synthetic pseudoceramides which can be applied to soaps, shampoos, cosmetic products, food and various emulsified systems, a process for preparing the same, and dermatologic external preparations containing the same.

2. Description of the Prior Art

According to recent investigations, the glycolipid of mammal cell is reported as playing an important role in functions as a reception, response and receptor of recognition and information, differentiation, proliferation, malignant change, or behavior of cells. The glycolipid belongs to the category of so-called sphingoglycolipid and comprises i) a basic lipid structure of ceramide in which fatty acid is bonded to sphingosine by a amide bond and ii) the combination of sugars selected from the group consisting of glucose, galactose, N-acetylglucosamine, fucose and cyalic acid which are bonded to the ceramide through glycoside bonds.

Ceramide is closely related to skin aging and resilience of skin, and it is well established that ceramide has a vital role in the production and maintenance of water permeability barrier of the skin. It is understood that the resilience and appearance of skin essentially relate to water content of several layers of skin. Collagen fiber of the inner skin, an essentail part to determine skin resilience, is bonded to water molecules, which proteoglycan also is bonded to lots of water molecules. As the water content of skin is determinded by diffusion of water from inner skin side, not by support of water from outside, the damage of lipid layer totally affects on the skin condition.

Ceramides are the most prominent lipids found in stratum corneum, the outermost layer of epidermis, and have an important function in formation and retention of stratum corneum. Skin damage caused by detergents which remove the lipids essential for the barrier function will result in an increased transdermal water loss(TEWL), and deteriorated barrier function has negative consequences for the total condition of the skin. Moreover, a damaged skin barrier leads to increased skin sensitivity and potential irritation such as atopic dermatitis or psoriasis. It has been found that topical applications of ceramide- or pseudoceramide-containing compositions are effective in relieving atopic eczema. They also have been found to exhibit therapeutic properties such as wound and ulcer healing through the promotion of cell restoration and growth.

With these reasons, many extentive efforts have been made by lots of the cosmetic and pharmaceutical companies to obtain access natural ceramide or pseudoceramide effectively. The proceses for preparing ceramides are widely divided into two categories: the one for processes by means of chemical synthesis, and the other for those by means of extraction from plants(WO 92/21321), animals[H. Lambers, et al., 2nd ASCS(1995), pp.106~125] or yeast(WO 94/10131). The present invention relates to processes by means of synthesis.

Synthetic processes are divided into two groups: the one for synthesizing ceramides which has the same structure as natural ceramides, and the other for synthesizing pseudoceramides which have similar structure to natural ceramides. In order to synthesize a pseudoceramide, it is preferable that the structure of natural ceramides should be examined first, and then ceramides having similar structure to natural ceramides should be synthesized. Natural ceramides existing in the nature are widely divided into 6 types, and the basic structure of these natural ceramides has at least two alkyl group, at least two hydroxy group and at least one amide bond.

EP 0282816(Kao, 1988) discloses a process for preparing pseudo ceramides wherein an easily substitutable glycidyl ether is synthesized and then reacted with alkanolamine; and then fatty acid is bonded thereto by an amide bond. When a pseudoceramide is prepared according to the process, it is disadvantageous in that the glycidyl ether having epoxide group must be synthesized as it is not a commonly used compound. Further, the process required at least three step reactions to obtain final pseudoceramides.

In U.S. Pat. No. 5,221,757(Kao, 1993), disclosed are processes for preparing various pseudoceramides through 2~6 step reactions by using glycidyl ether, ethanolamine and fatty acid ester substituted with hydroxy group as starting materials.

The pseudoceramides according to the above-mentioned patents have ether bonds which are not be found in natural ceramides, and some of them do not have amide bond. In addition, these patents are disadvantageous in that the process for preparation is relatively complicated and requires high production cost.

WO 92/06982(Unilever, 1992) discloses the preparation of pseudoceramides having two different general forms, and their application to cosmetic compositions. The pseudoceramides described in the patent are characterized in that the hydroxy group has been transformed by phosphorylation or sulfation of the compounds having similar basic skeleton to those of EP 0282816. However, this process also is disadvantageous in that the process for preparation requires many steps and much cost.

WO 92/03129(Duke Univ., 1992) discloses an invention relating to pseudoceramides having a basic structure of natural ceramides. However, the patent was limited in itsindustrial use.

SUMMARY OF THE INVENTION

The object of the present invention is to solve the problems of conventional arts described above and provide pseudoceramides satisfying the basic structure of natural ceramides.

Another object of the present invention is to provide a process for preparing compounds satisfying the basic structure of natural ceramides, which can very effectively prepare pseudoceramides by one or two step reaction(s) depending on the starting material and/or object material.

Further another object is to provide dermatologic external preparations for skin, which contains pseudoceramide compounds satisfying the basic structure of natural ceramides.

DETAILED DESCRIPTION OF THE INVENTION

Now, the pseudoceramides according to the present invention are described in detail.

The pseudoceramides according to the present invention have a basic structure of formula(I) or (II):

$$R_1\text{—COCHR}_2\text{CONR}_3R_4 \qquad (I)$$

$$R_1\text{---}CH(OH)CHR_2CONR_3R_4 \quad (II)$$

wherein, each of $R_1$ and $R_2$ represents linear or branched alkyl group or alkenyl group having 6~22 carbon atoms; each of $R_3$ and $R_4$ represents hydrogen, methyl, ethyl, propyl, or linear or branched $C_2$~$C_6$ alkyl group having one or more hydroxyl group(s).

The pseudoceramides represented by above formulas have two alkyl groups, one or more hydroxyl group(s) and one amide bond to satisfy the basic structure of natural ceramides. In the formulas, each of $R_1$ and $R_2$ represents linear or branched alkyl group or alkenyl group having 6~22 carbon atoms, preferably 12~20 carbon atoms, and more preferably 16~18 carbon atoms. Each of $R_3$ and $R_4$ represents hydrogen, methyl, ethyl, propyl, or linear or branched $C_2$~$C_4$ alkyl group having one or more hydroxyl group(s). $R_3$ and $R_4$ may be identical to or different from each other. The compounds of formula(I) or formula(II) have one or more hydroxy group(s), and the pseudoceramides represented by formula(II) is obtained by reducing the pseudoceramides represented by formula (I).

The compounds satisfying above formula(I) or (II) are listed in the Table below:

TABLE 1

| | Compound (I) | Compound (II) |
|---|---|---|
| 1 | (N,N-diethanol)-2-tetradecyl-3-oxostearamide | N,N-diethanol-2-tetradecyl-3-hydroxystearamide |
| 2 | N-methyl-N-(2,3,4,5,6-pentahydroxyhexyl)-2-tetradecyl-3-oxostearamide | N-methyl-N-(2,3,4,5,6-pentahydroxyhexyl)-2-tetradecyl-3-hydroxystearamide |
| 3 | N-(3-D-glucosyl)-2-tetradecyl-3-oxostearamide | N-(3-D-glucosyl)-2-tetradecyl-3-hydroxystearamide |
| 4 | N-(2,3-dihydroxypropyl)-2-tetradecyl-3-oxostearamide | N-(2,3-dihydroxypropyl)-2-tetradecyl-3-hydroxystearamide |
| 5 | N-(1,3-dihydroxyisopropyl)-2-tetra-decyl-3-oxostearamide | N-(1,3-dihydroxyisopropyl)-2-tetra-decyl-3-hydroxystearamide |
| 6 | N-(2,3,4,5,6-pentahydroxyhexyl)-2-tetradecyl-3-oxostearamide | N-(2,3,4,5,6-pentahydroxyhexyl)-2-tetradecyl-3-hydroxystearamide |

TABLE 1-continued

| | Compound (I) | Compound (II) |
|---|---|---|
| 7 | N-(2-methyl-1,3-dihydroxyisopropyl)-2-tetradecyl-3-oxostearamide | N-(2-methyl-1,3-dihydroxyisopropyl)-2-tetradecyl-3-hydroxystearamide |
| 8 | N-(2-ethyl-1,3-dihydroxyisopropyl)-2-tetradecyl-3-oxostearamide | N-(2-ethyl-1,3-dihydroxyisopropyl)-2-tetradecyl-3-hydroxystearamide |
| 9 | N-ethanol-2-tetradecyl-3-oxo-stearamide | N-ethanol-2-tetradecyl-3-hydroxy-stearamide |

The pseudoceramides of the above Table are synthesized by reacting alkylketene dimers with alkanolamines having one or more hydroxy group.

The details of synthesis of alkylketene dimers have been described in literatures such as *J. Amer. Chem. Soc.,* 5191 (1965), *J. Amer. Chem. Soc.,* 2444(1947) and *J. Amer. Chem. Soc.,* 1461(1950). Alternatively, commercially available alkylketene dimers(produced by BASF or Nippon Yushi) may be used. Alkylketene dimers may be used upon synthesizing by reacting acyl chlorides having desirable alkyl or alkenyl group with triethyl amine. The acyl chlorides are commercially available from several companies such as Aldrich, Fluka Sigma and Merck.

The alkyl group comprises 6~22 carbon atoms, preferably 12~20 carbon atoms, and more preferably 16~18 carbon atoms. When preparing an alkylketene dimer, two or more different kinds of acyl chlorides having different numbers of carbon may be used to prepare an alkylketene dimer which have been dimerized by different kinds having different number of carbon.

When acyl chloride is prepared starting from natural fatty acid, alkylketene dimers having various carbon distribution due to natural fatty acid may be synthesized, and alkylketene dimers comprising not only saturated hydrocarbons but also unsaturated hydrocarbons can be prepared. These, too, are usually called "alkylketene dimers", which are also included in the concept of "alkylketene dimers" described here-in-below.

In the process for preparing the pseudoceramides according to the present invention, usable amines are alkanolamines having one or more hydroxy group. Primary or secondary amines may be used.

Alkanolamines include 1-amino-2-propanol, 2-amino-1-propanol, 3-amino-1-propanol, 2-(methylamino)ethanol, 1-amino-2-butanol, 2-amino-1-butanol, 3-amino-1-butanol, 4-amino-1-butanol, 2-amino-2-methyl-1-propanol, 2-(ethylamino)ethanol, 2-amino-3-methyl-1-butanol, 1-amino-2-pentanol, 2-amino-1-pentanol, 5-amino-1-pentanol, 2-(propylamino)ethanol, 1-amino-2-hexanol, 2-amino-1-hexanol, 6-amino-1-hexanol, diethanolamine, 3-amino-1,2-propanediol, 2-amino-1,3-propanediol, 2-amino-2-methyl-1,3-propanediol, 2-amino-2-ethyl-1,3-propanediol, 2-amino-2-hydroxymethyl-1,3-propanediol, N-2,3,4,5,6-pentahydroxyhexylamine, or the like. In case of using a tertiary amine, it is disadvantageous that the obtained compound can be easily decomposed by water or the like as the obtained compound is not a stable amide, but a compound having an electric charge. Solvents which are usable in the preparation of the pseudoceramides include toluene, benzene, xylene, chloroform, methylene chloride, absolute alcohol, DMF(N,N-dimethylformamide), or the like. Among these, toluene is preferably used. When alcohol is used as a solvent, it is thought that the alkylketene dimer firstly reacts with alcohol to form an intermediate, β-ketoester, and then the reaction between the alkylketene dimer and the alkanolamine occurs. In this case, it is not desirable because separation of layers occurs during the reaction to lower the yield of the objective pseudoceramide compounds.

The processes for preparing pseudoceramides are proceeded under reflux condition of the reaction solvent, so that the reaction temperature essentially depends upon the type of reaction solvent.

In case that toluene is used as a reaction solvent, the reaction may be performed at a temperature between 50° C. and 110° C., and most preferably at 110° C., the reflux temperature of toluene.

Firstly, pseudoceramide(I) is synthesized by reaction of an alkylketene dimer with an alkanolamine or an amine derivative of a monosaccharide.

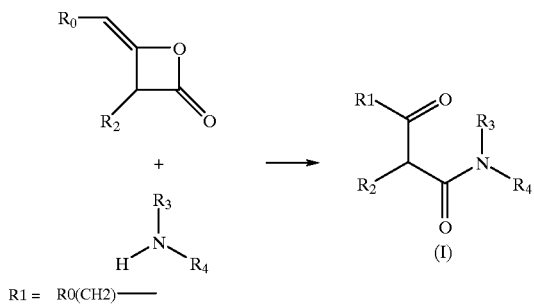

R1 = RO(CH2)—

In the reaction, the molar ratio of the alkylketene dimer and the amine is 1:1 to 1:2, preferably 1:1.1 to 1:1.5. The theoritical ratio of alkylketene dimer to amine is 1:1 by mole. When alkylketene dimer remains after the reaction, the removal is difficult to carry out, while the remained amine can be easily removed by using water or alcohol. Thus, it is preferable that the amount of amine should be more than that of alkylketene dimer so that the reaction completely consumes the alkylketene dimer.

The pseudoceramides(I), have basic structure of natural ceramides as they are, i.e. two or more alkyl groups, one amide bond and one or more hydroxy group(s). As the number of hydroxy group in the ceramide structure can substantially affect moisture-retaining property, it is possible that pseudoceramides(II) of novel type is synthesized by reducing the ketone group at β-position of the above-obtained pseudoceramide(I).

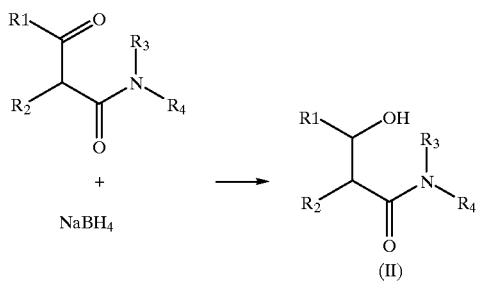

As illustrated above, pseudoceramides(I) can be converted to pseudoceramides(II) by reduction. Reducing agents which can be used in the reduction reaction include $NaBH_4$, $LiAlH(O-t-Bu)_3$, $BH_3$, 9-BBN(9-borabicyclo [3.3.1]nonane), $LiAlH_4$, and $AlH_3$. Among these, $LiAlH(O-t-Bu)_3$ or $NaBH_4$ is preferably used, and $NaBH_4$ is more preferable. When $NaBH_4$ is used as a reducing agent, methanol or ethanol was more effectively used as a solvent. In case of using methanol or ethanol as a solvent, it is advantageous in that additional solvent is not required in the crystallization step of the process for preparing pseudoceramides of formula(II).

Pseudo ceramides represented by formula(I) can be synthesized via only one-step reaction with very high yield in case of using a commercially available alkylketene dimer (produced by Nippon Yushi) as a starting material.

The compounds represented by formula(II) can be obtained by reducing the compounds represented by formula (I). In case of using commercially available alkylketene dimer as a starting material, the compounds(II) can be synthesized via two-step reactions. Thus, the process according to the present invention is more effective than any conventional process for preparing pseudoceramides.

The pseudoceramides according to the present invention may be used as an active component of dermatologic external preparations for skin. The dermatologic external preparations include cosmetic products such as lotion (nutrient emulsion), cream, astringent, essence oil, facial pack, wrinkle-preventing eye cream and cleansing products for removing make-up; hair care products such as shampoo, hair rinse, hair treatment lotion and hair conditioner; and body care products such as body cleanser, hand washer and soap.

When a pseudoceramide represented by formula(I) or (II) according to the present invention is incorporated in a cosmetic product, the amount of the compound is usually 0.00001~50% by weight of total weight of the cosmetic composition, preferably 0.001~20% by weight, and more preferably 0.1~10% by weight. If the compound is incorporated in a hair care products, the amount is usually 0.00001~20% by weight of total weight of the composition, preferably 0.001~10% by weight, more preferably 0.2~5.0% by weight. If it is applied to a body care products, the amount is usually 0.00001~30% by weight of total weight of the composition, preferably 0.001~15% by weight, and more preferably 0.1~5% by weight. If the content of the pseudoceramides is beyond the range described above, it is disadvantageous in that desirable formulation cannot be formed and the production cost will be increased.

PREFERRED EMBODIMENTS OF THE INVENTION

Now, The present invention is described with reference to Examples. As the present invention is to provide pseudoceramides having similar structure of natural ceramides, which usually have 16 or 18 carbon atoms, the examples mainly describes the synthesis of ceramides by using $C_{16}$-alkylketene dimer. However, it should not be noted that the present invention is restricted to those examples.

EXAMPLE 1

$C_{16}$-Alkylketene dimer(15 g, 31.5 mmol) and diethanolamine(4.97 g, 47.3 mmol) were used under toluene (20~50 ml) reflux system for about 10~24 hours. After adding about 200 ml of n-hexane and cooling this mixture, an off-white solid precipitated. The solid was purified from methanol or ethanol to give N,N-diethanol-2-tetradecyl-3-oxostearamide as off-white solid(yield: 30~50%). The physical properties of the obtained compound are shown below:

TLC($CHCl_3$:MeOH:AcOH=95:5:1):Rf=0.31 melting point: 85~87° C.

IR(vcm$^{-1}$, $CHCl_3$)3280, 2926, 2853, 1706, 1638, 1462

EXAMPLE 2

$C_{16}$-Alkylketene dimer(15 g, 31.5 mmol) and N-methyl-2,3,4,5,6-pentahydroxyhexylamine(8.0 g, 41.0 mmol) were used under toluene(20~50 ml) reflux system for about 24 hours. After adding about 200 ml of n-hexane and cooling this mixture, a white solid precipitated. The solid was purified from methanol to give N-methyl-N-(2,3,4,5,6-pentahydroxyhexyl)-2-tetradecyl-3-oxostearamide as white crystalline solid(yield: 60~80%). The physical properties of the obtained compound are shown below:

TLC($CHCl_3$:MeOH:AcOH=95:5:1):Rf=0.23 melting point: 88~90° C.

IR(vcm$^{-1}$, KBr) 3405, 2922, 2854, 1708, 1629, 1467

EXAMPLE 3

$C_{16}$-Alkylketene dimer(15 g, 31.5 mmol) and D-glucosamine (8.47 g, 47.3 mmol) were used under toluene (20~50 ml) reflux system for about 10~24 hours. After adding about 200 ml of n-hexane and cooling this mixture, a pale brown solid precipitated. The solid was purifird from methanol or ethanol to give N-(3-D-glucosyl)-2-tetradecyl-3-oxostearamide as yellowish solid(yield: 20~30%). The physical properties of the obtained compound are shown below:

TLC($CHCl_3$:MeOH:AcOH=95:5:1):Rf=0.20 melting point: 91~94° C.

IR($vcm^{-1}$, KBr) 3400, 2917, 2849, 1709, 1628, 1545, 1467

EXAMPLE 4

$C_{16}$-Alkylketene dimer(15 g, 31.5 mmol) and 3-amino-1,2-propanediol(3.16 g, 34.7 mmol) were used under toluene (20~50 ml) reflux system for about 3~24 hours. After adding about 200 ml of petroleum ether and cooling this mixture, a white solid precipitated. The solid was purified from methanol or ethanol to give N-(2,3-dihydroxypropyl)-2-tetradecyl-3-oxostearamide as white crystalline solid (yield: ≧90%). The physical properties of the obtained compound are shown below:

TLC($CHCl_3$:MEOH:AcOH=95:5:1):Rf=0.29 melting point: 84~85° C.

IR($vcm^{-1}$, KBr) 3312, 2918, 2849, 1716, 1636, 1540, 1467

EXAMPLE 5

$C_{16}$-Alkylketene dimer(15 g, 31.5 mmol) and N-(1,3-dihydroxyisopropyl)amine(3.16 g, 34.7 mmol) were used under toluene(20~50 ml) reflux system for about 3~24 hours. After adding about 200 ml of petroleum ether and cooling this mixture, a white solid precipitated. The solid was purified from methanol or ethanol to give N-(1,3-dihydroxyisopropyl)-2-tetradecyl-3-oxostearamide as white needle-like crystals (yield: ≧95%). The physical properties of the obtained compound are shown below:

TLC($CHCl_3$:MEOH:AcOH=95:5:1):Rf=0.24 melting point: 87~88° C.

IR($vcm^{-1}$, KBr) 3289, 2917, 2849, 1720, 1633, 1537, 1467

EXAMPLE 6

$C_{16}$-Alkylketene dimer(15 g, 31.5 mmol) and N-(2,3,4,5,6-pentahydroxyhexyl)amine(6.29 g, 34.7 mmol) were used under toluene(20~50 ml) reflux system for about 10~36 hours. After adding about 200 ml of n-hexane and cooling this mixture, an off-white solid precipitated. The solid was purified from methanol or ethanol to give N-(2,3,4,5,6-pentahydroxyhexyl)-2-tetradecyl-3-oxostearamide as pale yellow needle-like crystal (yield: 80~90%). The physical properties of the obtained compound are shown below:

TLC($CHCl_3$:MEOH:AcOH=95:5:1):Rf=0.23 melting point: 90~93° C.

IR($vcm^{-1}$, KBr) 3512, 3286, 2917, 2848, 1715, 1640, 1545, 1468

EXAMPLE 7

$C_{16}$-Alkylketene dimer(15 g, 31.5 mmol) and 2-amino-2-methyl-1,3-propanediol(3.65 g, 34.7 mmol) were used under toluene(20~50 ml) reflux system for about 3~24 hours. After adding about 200 ml of n-hexane and cooling this mixture, an off-white solid precipitated. The solid was purified from methanol or ethanol to give N-(2-methyl-1,3-dihydroxyisopropyl)-2-tetradecyl-3-oxostearamide, as white needle-like crystal (yield: ≧90%). The physical properties of the obtained compound are shown below:

TLC($CHCl_3$:MeOH:AcOH=95:5:1):Rf=0.30 melting point: 73~74° C.

IR($vcm^{-1}$, KBr) 3325, 2917, 2849, 1708, 1624, 1546, 1467

EXAMPLE 8

$C_{16}$-Alkylketene dimer(15 g, 31.5 mmol) and 2-amino-2-ethyl-1,3-propanediol(4.89 g, 41.0 mmol) were used under toluene(20~50 ml) reflux system for about 24~48 hours. After adding about 200 ml of n-hexane and cooling this mixture, an off-white solid precipitated. The solid was purified from methanol or ethanol to give N-(2-ethyl-1,3-dihydroxyisopropyl)-2-tetradecyl-3-oxostearamide, as white needle-like crystals (yield: ≧40~60%). The physical properties of the obtained compound are shown below:

TLC($CHCl_3$:MeOH:AcOH=95:5:1):Rf=0.35 melting point: 67~69° C.

IR($vcm^{-1}$, KBr) 3540, 3356, 2917, 2849, 1707, 1655, 1535, 1467

EXAMPLE 9

$C_{16}$-Alkylketene dimer(15 g, 31.5 mmol) and ethanolamine(2.12 g, 34.7 mmol) were used under toluene (20~50 ml) reflux system for about 10~15 hours. After adding 200 ml of n-hexane and cooling this mixture, an off-white solid precipitated. The solid was purified from methanol or ethanol to give N-ethanol-2-tetradecyl-3-oxostearamide, as white crystalline solid (yield: ≧90%). The physical properties of the obtained compound are shown below:

TLC($CHCl_3$:MeOH:AcOH=95:5:1):Rf=0.36 melting point: 83~87° C.

IR($vcm^{-1}$, KBr) 3272, 2910, 2848, 1715, 1656, 1530, 1470

EXAMPLE 10

The pseudoceramide(I) obtained from Example 4, N-(2,3-dihydroxypropyl)-2-tetradecyl-3-oxostearamide(5 g, 8.8 mmol) and some quantity of NaOH were placed under methanol(20 ml). While stirring and heating the reactant, sodium borohydride($NaBH_4$)(0.33 g, 8.8 mmol) was added thereto, and the mixture was refluxed for about 10 to 24 hours. Upon cooling, an off-white solid precipitated. The solid was purified from methanol to give N-(2,3-dihydroxypropyl)-2-tetradecyl-3-hydroxystearamide, as white needle-like crystals (yield: 50~70%). The physical properties of the obtained compound are shown below:

TLC($CHCl_3$:MeOH:AcOH=95:5:1):Rf=0.18 melting point: 96~97° C.

IR($vcm^{-1}$, KBr) 3289, 2925, 2854, 1642, 1547, 1467

EXAMPLE 11

The pseudoceramide(I) obtained from Example 5, N-(1,3-dihydroxyisopropyl)-2-tetradecyl-3-oxostearamide(5 g, 8.8 mmol) and some quantity of NaOH were placed under methanol(20 ml). While stirring and heating the reactant, sodium borohydride(NaBH$_4$)(0.33 g, 8.8 mmol) was added thereto, and the mixture was refluxed for about 10 to 24 hours. Upon cooling, an off-wite solid precipitated. The solid was purified from methanol to give N-(1,3-dihydroxyisopropyl)-2-tetradecyl-3-hydroxystearamide, as white needle-like crystals(yield: 50~70%). The physical properties of the obtained compound are shown below:

TLC(CHCl$_3$:MeOH:AcOH=95:5:1):Rf=0.19 melting point: 95~98° C.

IR(vcm$^{-1}$, KBr) 3277, 2923, 2851, 1637, 1535, 1467

EXAMPLE 12

The pseudoceramide(I) obtained from Example 7, N-(2-methyl-3-dihydroxyisopropyl)-2-tetradecyl-3-oxostearamide(5 g, 8.6 mmol) and some quantity of NaOH were placed under methanol(20 ml). While stirring and heating the reactant, sodium borohydride(NaBH$_4$) (0.32 g, 8.6 mmol) was added thereto, and the mixture was heated for about 10 to 24 hours. Upon cooling, an off-white solid precipitated. The solid was purified from methanol to give N-(2-methyl-1,3-dihydroxyisopropyl)-2-tetradecyl-3-hydroxystearamide, as white needle-like crystals(yield: 50~70%). The physical properties of the obtained compound are shown below:

TLC(CHCl$_3$:MeOH:AcOH=95:5:1):Rf=0.20 melting point: 87~89° C.

IR(vcm$^{-1}$, KBr) 3405, 2922, 2854, 1629, 1540, 1467

EXAMPLE 13

The pseudoceramide(I) obtained from Example 9, N-ethanol-2-tetradecyl-3-oxostearamide(5 g, 9.3 mmol) and some quantity of NaOH were placed under methanol(20 ml). While stirring and heating the reactant, sodium borohydride (NaBH$_4$)(0.35 g, 9.3 mmol) was added thereto, and the mixture was refluxed for about 10 to 24 hours. Upon cooling, an off-white solid precipitated. The solid was purified from methanol to give N-ethanol-2-tetradecyl-3-hydroxystearamide, as white crystalline solid (yield: 50~70%). The physical properties of the obtained compound are shown below:

TLC(CHCl$_3$:MeOH:AcOH=95:5:1):Rf=0.22 melting point: 108~112° C.

IR(vcm$^{-1}$, KBr) 3270, 2918, 2850, 1643, 1557, 1467

EXAMPLE 14

The aqueous phase comprising carbomer(Carbopol 940: produced by BF Goodrich in U.S.A.), propylene glycol, methyl dibromoglutaronitrile, phenoxyethanol, triethanolamine and purified water; and the oil phase comprising Ceteareth-25(Cremophor A 25: produced by BASF in Germany), glyceryl stearate, PEG-100 stearate(Myrj: produced by ICI in U.S.A.), stearic acid, isopropyl myristate, capric/caprylic triglyceride, propylene glycol dicaprylate/dicaprate, soysterol, myristic acid, and N-ethanol-2-tetradecyl-3-oxostearamide, were mixed with stirring at a temperature between 70° C. and 80° C. Stirring was continued until a homogeneous mixture was obtained, and the temperature was slowly lowered to prepare a homogeneous cream. The pH of the cream was adjusted to 6. The component ratio is listed in 5 Table 2.

TABLE 2

|   | Component | wt % |
|---|-----------|------|
| aqueous phase | carbomer | 0.34 |
|   | propylene glycol | 3.45 |
|   | methyl dibromoglutaronitrile | 0.1 |
|   | phenoxyethanol | 0.2 |
|   | triethanolamine | 1.62 |
| oil phase | Ceteareth-25 | 1.30 |
|   | glyceryl stearate | 2.00 |
|   | PEG-100 stearate | 1.25 |
|   | stearic acid | 1.30 |
|   | isopropyl myristate | 5.00 |
|   | capric/caprylic triglyceride | 7.00 |
|   | propylene glycol dicaprylate/dicaprate | 4.00 |
|   | soysterol | 0.50 |
|   | myristic acid | 0.50 |
|   | N-ethanol-2-tetradecyl-3-oxostearamide | 0.10 |
| others | perfume | 0.20 |
|   | purified water | 71.14 |

EXAMPLE 15

N-(2-methyl-1,3-dihydroxyisopropyl)-2-tetradecyl-3-oxostearamide, PEG-150 distearate(Kessco PEG 6000: produced by Stepan in U.S.A.), and polyquaternium-10 (Polymer JR 400: produced by Amerchol in U.S.A.) was melted by heating. 26% sodium laureth sulfate, 30% cocamidopropyl betaine, cocoyl diethanolamide, and decyl polyglucose were sequentially added to a vessel and mixed with stirring. Then, citric acid, perfume and preservative were sequentially added thereto with stirring. The pH was adjusted to 5.5 to prepare shampoo. The component ratio is listed in Table 3 below:

TABLE 3

| Component | wt % |
|-----------|------|
| 26% sodium laureth sulfate | 25 |
| 30% cocamidopropyl betaine | 15 |
| decyl polyglucose | 8 |
| PEG-150 distearate | 3 |
| cocoyl diethanolamide | 1 |
| polyquaternium-10 | 1 |
| N-(2-methyl-1,3-dihydroxyisopropyl)-2-tetradecyl-3-oxostearamide | 0.5 |
| citric acid | 0.2 |
| perfume | 0.5 |
| preservative | proper amount |
| purified water | balanced amount |

EXAMPLE 16

Stearyl alcohol and N-(2,3,4,5,6-pentahydroxyhexyl)-2-tetradecyl-3-oxostearamide was melted by heating. Hydroxyethyl cellulose, concentrated glycerine, cetyl trimethylammonium chloride, distearyl dimethylammonium chloride, dimethicone and lauryl dimethylamine oxide were sequentially added thereto and mixed with stirring. Then, citric acid, perfume and preservative were sequentially added thereto, and the pH was adjusted to 6 to prepare hair rinse. The component ratio is listed in Table 4 below:

TABLE 4

| Component | wt % |
|-----------|------|
| stearyl alcohol | 2 |
| N-(2,3,4,5,6-pentahydroxyhexyl)-2-tetradecyl-3-oxostearamide | 0.5 |

TABLE 4-continued

| Component | wt % |
|---|---|
| hydroxyethyl cellulose | 1 |
| concentrated glycerine | 5 |
| cetyl trimethylammonium chloride | 2 |
| distearyl dimethylammonium chloride | 0.4 |
| dimethicone | 1 |
| lauryl dimethylamine oxide | 1.5 |
| citric acid | 0.2 |
| perfume | 0.5 |
| preservative | proper amount |
| purified water | balanced amount |

EXAMPLE 17

The oil phase comprising N-methyl-N-(2,3,4,5,6-pentahydroxyhexyl)-2-tetradecyl-3-oxostearamide, cetostearyl alcohol, cetyl alcohol, stearyl stearate, dimethicone and squalane was melted at 70° C. with stirring. The aqueous phase comprising cetyl trimethylammonium chloride, hydroxyethyl cellulose, preservative and balance amount of water was mixed with the oil phase at 70~80° C. with stirring. Stirring was continued to obtain a homogeneous mixture, and then the temperature was lowered to prepare homogeneous hair treatment lotion. The component ratio is listed in Table 5.

TABLE 5

| | Component | wt % |
|---|---|---|
| oil phase | N-methyl-N-(2,3,4,5,6-pentahydroxy-hexyl)-2-tetradecyl-3-oxostearamide | 0.5 |
| | cetostearyl alcohol | 2 |
| | cetyl alcohol | 1 |
| | stearyl stearate | 3 |
| | dimethicone | 2 |
| | squalane | 1 |
| aqueous phase | cetyl trimethylammonium chloride | 1 |
| | hydroxyethyl cellulose | 1.5 |
| others | perfume | 0.5 |
| | preservative | proper amount |
| | purified water | balanced amount |

EXAMPLE 18

Myristic acid, palmitic acid, ethylene glycol stearate, glycerine and N-(2,3-dihydroxypropyl)-2-tetradecyl-3-oxostearamide were melted with heating to be dispersed. Potassium hydroxide solution was added thereto to carry out saponification by stirring at 70~80° C. While cooling the mixture, 26% sodium laureth sulfate, 30% cocamidopropyl betaine, cocoyl diethanolamide, citric acid, perfume and preservative are sequentially added thereto and mixed with stirring. Then, pH of the mixture was adjusted to 8.5 to prepare body cleanser. The component ratio is listed in Table 6 below:

TABLE 6

| Component | wt % |
|---|---|
| myristic acid | 8 |
| palmitic acid | 5 |
| ethylene glycol stearate | 3 |
| concentrated glycerine | 3 |
| N-(2,3-dihydroxypropyl)-2-tetradecyl-3-oxostearamide | 0.5 |

TABLE 6-continued

| Component | wt % |
|---|---|
| potassium hydroxide solution | 5 |
| 26% sodium laureth sulfate | 20 |
| 30% cocamidopropyl betaine | 15 |
| cocoyl diethanolamide | 3 |
| citric acid | 0.2 |
| perfume | 0.5 |
| preservative | proper amount |
| purified water | balanced amount |

EXAMPLE 19

To a cosmetic soap base, conventional ingredients of the following ratio were added and mixed. The mixture was extruded, molded and formed cosmetic soaps. The component ratio is listed in Table 7 below:

TABLE 7

| Component | wt % |
|---|---|
| soap base* | 98.15 |
| titanium dioxide | 0.3 |
| perfume | 1.0 |
| dye | 0.05 |
| N-ethanol-2-tetradecyl-3-hydroxystearamide | 0.5 |

*conventional soap base having 11.0% of moisture content

When the pseudoceramides according to the present invention are applied to dermatologic external preparations for skin, the moisture-retaining property and resilience of skin and hair become excellent, so that they are useful to prevent skin aging. Besides, the pseudoceramides induce formation of lipid layer on damaged skin and prevent the inhibition of lipid synthesis.

What is claimed is:

1. A pseudoceramide derivative represented by formula (I) or (II):

$$R_1\text{—COCHR}_2\text{CONR}_3R_4 \qquad (I)$$

$$R_1\text{—CH(OH)CHR}_2\text{CONR}_3R_4 \qquad (II)$$

wherein, each of $R_1$ and $R_2$ represents linear or branched alkyl group or alkenyl group having 6–22 carbon atoms; each of $R_3$ and $R_4$ represents hydrogen, methyl, ethyl, propyl, or linear or branched $C_2$–$C_6$ alkyl group having one or more hydroxyl group(s), or monosaccharide with the proviso that when either $R_3$ or $R_4$ is hydrogen, the other is not hydroxyethyl.

2. A process for preparing a pseudoceramide derivative represented by formula(II):

$$R_1\text{—CH(OH)CHR}_2\text{CONR}_3R_4 \qquad (II)$$

wherein, each of $R_1$ and $R_2$ represents linear or branched alkyl group or alkenyl group having 6~22 carbon atoms; each of $R_3$ and $R_4$ represents hydrogen, methyl, ethyl, propyl, or linear or branched $C_2$~$C_6$ alkyl group having one or more hydroxyl group(s), which comprises reducing a compound represented by formula (I):

$$R_1\text{—COCHR}_2\text{CONR}_3R_4 \qquad (I)$$

wherein, each of $R_1$, $R_2$, $R_3$ and $R_4$ is defined as above, by using a reducing agent.

3. A process for preparing a pseudoceramide derivative according to claim 2, wherein the reducing agent is a compound selected from a group consisting of NaBH$_4$, LiAlH(O-t-Bu)$_3$, BH$_3$, 9-BBN(9-borabicyclo[3.3.1]nonane), LiAlH$_4$, and AlH$_3$.

4. A process for preparing a pseudoceramide derivative represented by formula(I):

$$R_1\text{—COCHR}_2\text{CONR}_3\text{R}_4 \qquad (I)$$

wherein, each of R$_1$ and R$_2$ represents linear or branched alkyl group or alkenyl group having 6~22 carbon atoms; each of R$_3$ and R$_4$ represents hydrogen, methyl, ethyl, propyl, or linear or branched C$_2$~C$_6$ alkyl group having one or more hydroxyl group(s), which comprises reacting an alkylketene dimer with an alkanolamine in a molar ratio of 1:1~1:2 in the presence of a solvent.

5. A process for preparing a pseudoceramide derivative according to claim 4, wherein said alkanolamine is a compound selected from a group consisting of 1-amino-2-propanol, 2-amino-1-propanol, 3-amino-1-propanol, 2-(methylamino)ethanol, 1-amino-2-butanol, 2-amino-1-butanol, 3-amino-1-butanol, 4-amino-1-butanol, 2-amino-2-methyl-1-propanol, 2-(ethylamino)ethanol, 2-amino-3-methyl-1-butanol, 1-amino-2-pentanol, 2-amino-1-pentanol, 5-amino-1-pentanol, 2-(propyl amino)ethanol, 1-amino-2-hexanol, 2-amino-1-hexanol, 6-amino-1-hexanol, diethanolamine, 3-amino-1,2-propanediol, 2-amino-1,3-propanediol, 2-amino-2-methyl-1,3-propanediol, 2-amino-2-ethyl-1,3-propanediol, 2-amino-2-hydroxymethyl-1,3-propanediol, and 2,3,4,5,6-pentahydroxyhexylamine.

6. A dermatologic external preparation for skin, which comprises a pseudoceramide derivative represented by formula(I) or (II):

$$R_1\text{—COCHR}_2\text{CONR}_3\text{R}_4 \qquad (I)$$

$$R_1\text{—CH(OH)CHR}_2\text{CONR}_3\text{R}_4 \qquad (II)$$

wherein, each of R$_1$ and R$_2$ represents linear or branched alkyl group or alkenyl group having 6~22 carbon atoms; each of R$_3$ and R$_4$ represents hydrogen, methyl, ethyl, propyl, or linear or branched C$_2$~C$_6$ alkyl group having one or more hydroxyl group(s).

7. A dermatologic external preparation for skin according to claim 6, wherein the pseudoceramide derivative is present in an amount of 0.00001 to 50% by weight of total composition.

8. A dermatologic external preparation for skin according to claim 6, which is a cosmetic product, a hair care product or a body care product.

* * * * *